United States Patent
Fu et al.

(10) Patent No.: US 7,470,666 B2
(45) Date of Patent: Dec. 30, 2008

(54) USE OF ULINASTATIN AND ITS PHARMACEUTICAL COMPOSITION FOR TREATING SEVERE ACUTE RESPIRATORY SYNDROME

(75) Inventors: Heliang Fu, Guangdong (CN); Piqu Miao, Guangdong (CN); Xiaoyan Wang, Guangdong (CN); Yongli Xie, Guangdong (CN)

(73) Assignee: Guangdong Techpool Biochem. Pharma. Co., Ltd., Guangdong (CN)

( * ) Notice: Subject to any disclaimer, the term of this patent is extended or adjusted under 35 U.S.C. 154(b) by 0 days.

(21) Appl. No.: 10/558,226

(22) PCT Filed: May 25, 2004

(86) PCT No.: PCT/CN2004/000533

§ 371 (c)(1),
(2), (4) Date: Nov. 15, 2006

(87) PCT Pub. No.: WO2004/103399

PCT Pub. Date: Dec. 2, 2004

(65) Prior Publication Data

US 2007/0275879 A1    Nov. 29, 2007

(30) Foreign Application Priority Data

May 26, 2003    (CN)    ................ 03 1 25188

(51) Int. Cl.
*A61K 38/57*    (2006.01)
*A61K 38/16*    (2006.01)

(52) U.S. Cl. ............... 514/12; 514/2; 424/545

(58) Field of Classification Search ........ None
See application file for complete search history.

(56) References Cited

FOREIGN PATENT DOCUMENTS

| EP | 0 327 999 | * | 6/1992 |
| EP | 0327999 | | 6/1992 |
| JP | 2000336041 | | 12/2000 |
| JP | 20000335041 | * | 12/2000 |

OTHER PUBLICATIONS

Yin et al, "Protective effects of ulinastatin on acute lung injury induced by acute necrotizing pancreatitis in rats." Shijie Huaren Xiaohua Zazhi (2002), 10(5), 558-561 (Abstract only cited).*
Li et al, "Effects of ulinastatin on interleukin-8 during one-lung ventilation in surgery." Aizheng (2003), 22(10), 1074-1076 (Abstract only cited).*
Isobe et a, "Inhibition of tumor necrosis factor-a production by urinary trypsin inhibitor." International Congress Series (2003), 1255(Biological Response to Planned and Unplanned Injuries), 69-74 (Abstract only cited).*
Nicholls et al, "Lung pathology of fatal severe acute respiratory syndrome," Lancet, vol. 361, Issue 9371, May 24, 2003, pp. 1773-1778.*
Wong et al, "Plasma inflammatory cytokines and chemokines in severe acute respiratory syndrome." Clinical and experimental immunology Apr. 2004, 136 (1) p. 95-103.*
Ng et al, "Inflammatory cytokine profile in children with severe acute respiratory syndrome." Pediatrics Jan. 2004, 113 (1 Pt 1) pe7-14.*
Cai et al. Circulatory Shock 43(2): 71-78, 1994, abstract only cited.*
Manamiya et al. Sasshi Journal. Nihon Kyobu Geka Gakkai 41(12): 2364-2371, abstract only cited.*
Manamiya et al. Sasshi Journal. Nihon Kyobu Geka Gakkai 41(12): 2364-2371, abstract only cited. (2003).*
Cai, Ming et al., "Effects of Free Radical Scavengers, Methylprednisolone, and Ulinastatin on Acute Xanthine and Xanthine Oxidase-Induced Lung Injury in Rats," Dept. of Anesthesiology, Nippon Med. School, Tokyo, Japan, pp. 71-78, 1994.

* cited by examiner

*Primary Examiner*—Mary E Mosher
(74) *Attorney, Agent, or Firm*—Ohlandt, Greeley, Ruggiero & Perle, LLP; George W. Rauchfuss, Jr.; Charles N.J. Ruggiero

(57) ABSTRACT

The present invention relates to use of Ulinastatin and its pharmaceutical composition for treating and/or preventing Severe Acute Respiratory Syndrome (SARS). Ulinastatin is effective for treating and/or preventing SARS, particularly Acute Lung Injury (ALI) or Acute Respiratory Distress Syndrome (ARDS). Ulinastatin is generally used as the pharmaceutical composition, preferably in the form of freeze-dried powder or aqueous solution for injection.

6 Claims, No Drawings

USE OF ULINASTATIN AND ITS PHARMACEUTICAL COMPOSITION FOR TREATING SEVERE ACUTE RESPIRATORY SYNDROME

FIELD OF THE INVENTION

The present invention relates to a pharmaceutical field, and more specificially, the invention relates to a new medical use of Ulinastatin for the treatment and/or prevention of Severe Acute Respiratory Syndrome (SARS).

BACKGROUND OF THE INVENTION

Severe Acute Respiratory Syndrome (SARS) (also referred to as "atypical pneumonia") brings about a severe threat to human life. The World Health Organization (WHO) recognizes that Severe Acute Respiratory Syndrome (SARS) is a disease caused by a variant of subtype of Coronavirus, i.e. SARS virus and exhibits clinically an inflammatory reaction. Acute Lung Injury (ALI) or Acute Respiratory Distress Syndrome (ARDS) emerges when the disease worsens.

Ulinastatin is a glycoprotein isolated from human urine, and is also called human urine trypsin inhibitor (UTI). Ulinastatin is first marketed in Japan in 1985 and has been used as a medicament for the treatment of acute pancreatitis, acute circulatory failure and shock. Animal experiments have demonstrated that Ulinastatin possesses a variety of special pharmacological properties. For example, Ulinastatin may be used to improve immunologic function and protect visceral function. SHINYA MURAKAMI et al. reported that Ulinastatin not only inhibited various serine proteinase such as trypsin, α-chymotrypsin, fibrinolysin and multinuclear granulocyte elastase, but also inhibited the release of inflammation mediators from leukocyte such as TNF-α, IL-1 and IL-6 and the release of oxygen free radical (Tissue Culture Engineering, 2001, 27(9), p. 348-354). It is currently known that multinuclear granulocyte elastase, inflammation mediator and oxygen free radical are involved in the pathogenesis of Acute Lung Injury (ALI) or Acute Respiratory Distress Syndrome (ARDS). The inventor of the application has conducted intensive clinical studies and found that Ulinastatin is highly effective for the treatment of Severe Acute Respiratory Syndrome (SARS), and particularly for the treatment of Acute Lung Injury (ALI) or Acute Respiratory Distress Syndrome (ARDS) induced by SARS.

DISCLOSURE OF THE INVENTION

The object of the present invention is to provide use of Ulinastatin for the treatment and/or prevention of Severe Acute Respiratory Syndrome (SARS), i.e. a use for preparation of medicaments for the treatment and/or prevention of Severe Acute Respiratory Syndrome (SARS).

Another object of the present invention is to provide a pharmaceutical composition comprising Ulinastatin as active ingredient for the treatment and/or prevention of Severe Acute Respiratory Syndrome (SARS).

According to the present invention, Ulinastatin is highly effective for the treatment of Severe Acute Respiratory Syndrome (SARS) caused by SARS virus, and particularly for the treatment of Acute Lung Injury (ALI) or Acute Respiratory Distress Syndrome (ARDS) induced by SARS virus.

According to the present invention, Ulinastatin is generally used as pharmaceutical composition comprising a therapeutically effective amount of Ulinastatin as active ingredient and a pharmaceutically acceptable adjuvant. The pharmaceutical composition comprising Ulinastatin is typically administrated by intravenous injection in a form of freeze-dried powder for injection and/or injection.

According to the present invention, the pharmaceutical composition comprising Ulinastatin as active ingredient for i.v. injection is generally administered in a form of solid sterilized composition, which may contain additional additives such as mannitol, lactose, hydrolyzed gelatin, sodium chloride and glucose. The solid composition is dissolved into sterilized water or other sterilized media for injection.

According to the present invention, the pharmaceutical composition comprising Ulinastatin as active ingredient for i.v. injection may also be administered in a form of aqueous solution. The aqueous solution may contain additives such as mannitol, sodium chloride and glucose.

The preparation method of freeze-dried powder of Ulinastatin for injection may include following steps: An aqueous solution of Ulinastatin sterilized by filtration (100,000,000 units) is added to 20 g of mannitol; After dissolution, the solution is adjusted to a neutral pH and 2000 ml of water for injection is added; After addition of sodium chloride for isotonic adjustment, the solution is filtered for sterilization, dispensed into 1000 vials and freeze-dried under an aseptic condition.

The preparation method of aqueous solution of Ulinastatin for injection may include following steps: An aqueous solution of Ulinastatin sterilized by filtration (100,000,000 units) is added to 20 g of mannitol; After dissolution, the solution is adjusted to a neutral pH and 2000 ml of water for injection is added; After addition of sodium chloride for isotonic adjustment, the solution is filtered under an aseptic condition and dispensed into 1000 vials.

The present invention also relates to a method for the treatment of Severe Acute Respiratory Syndrome (SARS) by administering a therapeutically effective amount of Ulinastatin, wherein the dosage of Ulinastatin varies with the severity of the disease and the phase of treatment. Typically, 300-3000 thousands of units of Ulinastatin is administrated by intravenous injection each time, 1-4 times per day.

Generally, an appropriate dosage is determined on the basis of the disease severity and other factors of the subject to be treated.

EXAMPLE

The therapeutic effect of Ulinastatin on Severe Acute Respiratory Syndrome (SARS) was demonstrated by following clinical experiments.

Thirty-six patients of Severe Acute Respiratory Syndrome (SARS) were equally divided into two groups (18 patients per group), i.e. the Ulinastatin treatment cure group and the control group. In the control group, a standard treatment scheme (antiviral treatment, anti-inflammatory treatment, glucocorticoid treatment, immunopotentiator treatment and supporting treatment) was adopted, wherein oxygen was supplied by nasal tube or face mask with a flow rate of 6 liters per minute and a non-traumatic respirator treatment was adopted when saturation oxygen in blood was lower than 96%. In the Ulinastatin treatment group, 300,000 units of Ulinastatin were administrated by intravenous injection every 8 hours and otherwise the procedure is the same as that in the control group. Before the Ulinastatin treatment, the gender, age, APACHE II score, respiratory frequency, oxygenation index ($PaO_2/FiO_2$) and $PaCO_2$ of the patients between the two groups did not show a statistically significant difference (Table 1). After the Ulinastatin treatment, however, the respiratory frequency, the change of chest photograph and $PaCO_2$ of the patients between the two groups showed a statistically significant difference even though the $PaO_2/FiO_2$ did not differ significantly between the two groups, (Table 2). Four patients in the control group died while only one patient in the treatment group died (Table 3).

TABLE 1 the comparison of indexes between the treatment group and the control group before Ulinastatin treatment

| Item | Treatment group | Control group | T value | P value |
|---|---|---|---|---|
| Gender (man/woman) | 6/12 | 5/13 | | |
| Age | 42.22 ± 14.87 | 37.56 ± 9.78 | 1.11 | 0.27 |
| APACHE II | 11.28 ± 5.96 | 9.06 ± 2.26 | 1.48 | 0.15 |
| Respiratory frequency | 32.67 ± 2.43 | 32.22 ± 3.19 | 0.47 | 0.64 |
| $PaO_2/FiO_2$ | 195.89 ± 24.84 | 195.44 ± 31.42 | 0.47 | 0.96 |
| $PaCO_2$ | 30.17 ± 1.76 | 30.85 ± 2.09 | 1.04 | 0.31 |

TABLE 2 the comparison of indexes between the treatment group and the control group after Ulinastatin treatment

| Item | Treatment group | Control group | T value | P value |
|---|---|---|---|---|
| Respiratory frequency | 23.89 ± 3.32 | 28.39 ± 5.62 | 2.93 | 0.006 |
| $PaO_2/FiO_2$ | 306.56 ± 57.46 | 258.39 ± 87.68 | 1.95 | 0.06 |
| $PaCO_2$ | 37.22 ± 3.06 | 35.22 ± 2.36 | 2.19 | 0.035 |
| Change of chest photograph | 2.94 ± 0.54 | 2.00 ± 1.24 | 2.97 | 0.007 |

TABLE 3 the comparison of mortality between the treatment group and the control group after Ulinastatin treatment

| Group | Survival | Death | Sum |
|---|---|---|---|
| Administration group | 17 | 1 | 18 |
| Control group | 14 | 4 | 18 |

$X^2 = 0.929, P = 0.335$

Typical Case

Ms. Liu, a female patient of 47 years old, was diagnosed to be affected with Severe Acute Respiratory Syndrome (SARS) and hospitalized in April 2003. The symptoms of Ms. Liu were as follows: high temperature up to 39° C., chest distress, suffocated, dyspnea and soreness in whole body. The results of body check were as follows: HR, 118 per minute; RR, 35 per minute; BP, 130/65 mmHg with a mental dysphoria. The chest photograph showed that there was a widespread spotted infiltration shadow in middle and lower parts of right lung while there was a dispersed infiltration shadow in lower part of left lung. The APACHE II score was 13. During the first 10 days of hospitalization, the exacerbation occurred even after the antiviral treatment, anti-inflammatory treatment, glucocorticoid treatment and supporting treatment and the patient needed a non-traumatic respirator to aerate (arterial blood gas analysis: pH, 7.51; $PaO_2$, 53 mmHg; $PaCO_2$, 28 mmHg; $SPO_2$: 91%). At this point, 300,000 units of Ulinastatin was administrated by intravenous injection every 8 hours. Five days later, the feel of chest distress and suffocation in patient was alleviated, and arterial blood gas analysis showed an increase both in $PaO_2$ and $PaCO_2$. Ten days later, vital signs of the patient further ameliorated. The chest photograph validated that the pathological change in right lung was assimilated significantly and the pathological change in lower part of left lung disappeared.

These results showed that Ulinastatin is capable of treating and/or preventing Severe Acute Respiratory Syndrome (SARS) caused by SARS virus, and particularly Acute Lung Injury (ALI) or Acute Respiratory Distress Syndrome (ARDS) induced by SARS virus.

What is claimed is:

1. A method for the treatment of Severe Acute Respiratory Syndrome, comprising administering a therapeutically effective amount of Ulinastatin.

2. A method for the treatment of Severe Acute Respiratory Syndrome, comprising administrating a therapeutically effective amount of a pharmaceutical composition having a therapeutically effective amount of Ulinastatin as active ingredient and a pharmaceutically acceptable additive.

3. The method according to claim 2, wherein the pharmaceutical composition is a freeze-dried powder dissolved in water or other media.

4. The method according to claim 2, wherein the pharmaceutical composition is an aqueous solution.

5. The method according to claim 1, wherein the administering step comprises injecting the therapeutically effective amount of Ulinastatin.

6. The method according to claim 2, wherein the administering step comprises injecting the therapeutically effective amount of the pharmaceutical composition.

* * * * *